United States Patent
Bahi et al.

(10) Patent No.: US 11,103,808 B2
(45) Date of Patent: Aug. 31, 2021

(54) PROCESS FOR RECOVERING ISOPRENOIDS PRODUCED BY MICROORGANISMS

(71) Applicants: TOTAL RAFFINAGE CHIMIE, Courbevoie (FR); AMYRIS, INC., Emeryville, CA (US)

(72) Inventors: Maha Bahi, Saint Germain en Laye (FR); Anthony Hutin, Vannecrocq (FR); Fernando Leal-Calderon, La Brède (FR)

(73) Assignee: Amyris, Inc., Emeryville, CA (US)

( * ) Notice: Subject to any disclaimer, the term of this patent is extended or adjusted under 35 U.S.C. 154(b) by 0 days.

(21) Appl. No.: 16/637,059

(22) PCT Filed: Aug. 1, 2018

(86) PCT No.: PCT/EP2018/070844
§ 371 (c)(1),
(2) Date: Feb. 6, 2020

(87) PCT Pub. No.: WO2019/030073
PCT Pub. Date: Feb. 14, 2019

(65) Prior Publication Data
US 2020/0179824 A1 Jun. 11, 2020

(30) Foreign Application Priority Data
Aug. 7, 2017 (EP) .................... 17306050

(51) Int. Cl.
*C12P 1/02* (2006.01)
*B01D 17/04* (2006.01)
*C12P 5/00* (2006.01)

(52) U.S. Cl.
CPC ............ *B01D 17/047* (2013.01); *C12P 5/007* (2013.01)

(58) Field of Classification Search
CPC ................ C12P 5/007; C12P 5/02; C12P 1/02
See application file for complete search history.

(56) References Cited

U.S. PATENT DOCUMENTS

2011/0295028 A1   12/2011   Cherinko et al.

FOREIGN PATENT DOCUMENTS

| | | |
|---|---|---|
| WO | 2006014837 A1 | 2/2006 |
| WO | 2007140339 A2 | 12/2007 |
| WO | 2008039499 A2 | 4/2008 |
| WO | 2010115074 A1 | 10/2010 |
| WO | 2012024186 A1 | 2/2012 |
| WO | 2012028186 A1 | 3/2012 |
| WO | 2013071172 A1 | 5/2013 |
| WO | 2014144135 A2 | 9/2014 |

OTHER PUBLICATIONS

Cuellar et al, "Recent advantages in the microbial production and recovery of apolar molecules", Current Opinion in Biotechnology, (2015), vol. 33, pp. 39-45.

Benjamin et al, "Developing commercial production of semi-synthetic artemisinin, and of beta-famesene, an isoprenoid produced by fermentation of Brazilian sugar", Journal of the Brazilian Chemical Society, (2016), vol. 27, pp. 1339-1345.

Heeres et al, "Microbial advanced biofuels production: overcoming emulsification challenges for large-scale operation", Trends in Biotechnology, (2014), vol. 32, pp. 221-229.

Anghelache et al, "Rheological properties and stability of squalene emulsion prepared with non-ionic emulsifier", Revista De Chimie, (Aug. 2017), vol. 68, pp. 1681-1684.

Tedyono, "Extraction of phenolic compounds from aqueous solution using a slightly hydrophobic nonionic surfactant Tergitol 15-S-5", Summary of a thesis, (2009), pp. 1-6, National Cheng Kung University, Taiwan URL: http://etds.lib.ncku.edu.tw/etdservice/view_metadata?etdun=U0026-0812200915265880, (Sep. 21, 2017).

International Search Report issued in Application No. PCT/EP2018/070844, dated Aug. 31, 2018; 4 pages.

*Primary Examiner* — Tekchand Saidha
(74) *Attorney, Agent, or Firm* — Andrew W. Shyjan

(57) ABSTRACT

The present invention is a process for recovering an isoprenoid compound produced by fermentation from a fermentation medium comprising:

(a) demulsifying the fermentation medium or a fraction thereof in presence of a salt and a surfactant, thereby generating a stream having an organic phase containing the isoprenoid compound and a phase heavier than the organic phase, and (b) separating the stream obtained in step (a) into the organic phase containing the isoprenoid compound, the phase heavier than the organic phase, and optionally a solid phase containing host cell debris and cells.

12 Claims, 2 Drawing Sheets

PROCESS FOR RECOVERING ISOPRENOIDS PRODUCED BY MICROORGANISMS

CROSS-REFERENCE TO RELATED APPLICATIONS

This application claims the benefit of PCT/EP2018/070844 filed Aug. 1, 2018, which claims priority from EP 17306050.0 filed Aug. 7, 2017, which are incorporated herein by reference in their entireties for all purposes.

FIELD OF THE INVENTION

The present invention relates to the recovery of an isoprenoid produced by microorganisms. In particular, the invention provides methods for recovering a sesquiterpene such as farnesene, in particular β-farnesene produced by a microorganism. The invention accordingly relates to the fields of biology, microbiology, fermentation technology and oil and fuel production technology.

BACKGROUND OF THE INVENTION

The microbial production of bio-organic compounds such as farnesene is known in the art. The fermentation products produced in the microbial cells may be present in the culture supernatant and/or associated with the microbial cells. A problem encountered in the microbial fermentation of bio-organic compounds is that it is difficult to recover the bio-organic compounds from the fermentation mixture. Separation of the bio-organic compound from the fermentation mixture often relies on the use of a surfactant to break emulsions comprising the bio-organic compound. However, adding a surfactant has a cost and the surfactant becomes an impurity that has to be removed downstream in the process. Moreover, some emulsions are not broken by addition of a surfactant and some emulsions are only partly broken by addition of a surfactant.

In particular, stability of emulsions containing an isoprenoid compound as bio-organic compound makes difficult to recover a maximum of isoprenoid compound. It is usually necessary to use large quantities of surfactants to destabilize the emulsion and recover the isoprenoid compound.

WO2012028186 discloses a method for purifying bio-organic compounds from fermentation broth containing surfactants by temperature-induced phase inversion. The method relies on first forming a chemically defined emulsion in an aqueous medium such as the fermentation broth. The formation of this emulsion is mediated by the addiction of a surfactant whose solubility in an aqueous medium decreases with increasing temperature and the temperature of the aqueous medium is below its phase inversion temperature or cloud point. The resulting emulsion is then destabilized by increasing the temperature of the composition to above its phase inversion temperature or cloud point. The phase inversion temperature is the temperature at which the continuous and dispersed phases of an emulsion system are inverted (e.g. an oil-in-water emulsion becomes a water-in-oil emulsion or vice-versa). The cloud point refers to the temperature at which one or more liquids and/or solids dissolved in a fluid are no longer completely soluble, precipitating as a second phase giving the fluid a cloudy appearance.

US2011295028A1 discloses processes for obtaining a lipid from a cell by lysing the cell, contacting the cell with a base and/or salt, and separating the lipid. The disclosed processes include raising the pH of the cell composition to 8 or above and separating lipid from the cell composition. Addition of a salt in this pH range allows demulsification of the solution containing the lipid. This document only concerns lipid-containing microorganisms for which the lipid recovery necessitates to rupture the cell wall and/or cell membrane to release their cytoplasmic content including the lipids. The emulsion to demulsify does not contain any isoprenoic compound but only fatty acids or esters of fatty acids (like triglycerides).

There is therefore a need for a process allowing recovering an isoprenoid compound from a culture medium in high yields using reduced amounts of surfactants.

BRIEF SUMMARY OF THE INVENTION

An object of the present invention is a process for recovering an isoprenoid compound produced by fermentation from a fermentation medium, comprising:

(a) demulsifying the fermentation medium or a fraction thereof in presence of a salt and a surfactant, thereby generating a stream having an organic phase containing the isoprenoid compound and a phase heavier than the organic phase, and (b) separating the stream obtained in step (a) into the organic phase containing the isoprenoid compound, the phase heavier than the organic phase, and, optionally, a solid phase containing host cell debris and cells.

The process of the invention allows recovering of isoprenoid compound(s) from emulsion.

The recovery process of the invention does not require any monitoring of the temperature above or below a phase inversion temperature or cloud point to allow recovering isoprenoid compounds.

In one embodiment, the presence of the salt and surfactant in the demulsifying step (a) results from addition of the salt and surfactant, the salt being at a concentration of 0.01 mol/L or more.

In some embodiments, no acid or base is added to the fermentation medium or the fraction thereof prior or during the demulsifying step (a). In other words, no compound capable of raising or lowering the pH of the fermentation medium is added.

In some embodiments, in the demulsifying step (a), the pH range of the fermentation medium or the fraction thereof is from 2 to 7.

In some embodiments, the surfactant is selected from an anionic surfactant and a non-ionic surfactant and their mixture. In a preferred embodiment, the anionic surfactant is selected from sulfates and sulfonates and the non-ionic surfactant is a polyether polyol. Both are preferably soluble in water at room temperature (20° C.).

In some embodiments, the concentration of surfactant in the fermentation medium or the fraction thereof in the demulsifying step (a) is from $5 \cdot 10^{-3}$ to 1% v/v.

In some embodiments, the concentration of salt in the fermentation medium or the fraction thereof in the demulsifying step is from 0.01 mol/L to 5 mol/L or from 0.05 mol/L to 4.5 mol/L, or from 0.1 mol/L to 4 mol/L, or from 0.5 to 3 mol/L.

In some embodiments, the separation step (b) is a liquid/liquid separation.

In some embodiments, the fermentation medium or the fraction thereof is heated before being submitted to the separation step (b), preferably after addition of the surfactant, at a heating temperature inferior to a temperature at which the isoprenoid compounds are degraded or decomposed.

The invention also provides a method for the recovery of isoprenoid compounds as fermentation products from a fermentation medium comprising the following steps:
optionally separating the fermentation medium into a solid/liquid light phase and a solid/liquid heavy phase,
adding a salt and a surfactant to the fermentation medium or the solid/liquid light phase, thereby generating an organic phase containing the isoprenoid compound and a phase heavier than the organic phase,
separating the organic phase containing the isoprenoid compound from the phase heavier than the organic phase.

The separation of the organic phase containing the isoprenoid may be a liquid/liquid separation.

In a preferred embodiment, the separation of the fermentation medium into a solid/liquid light phase and a solid/liquid heavy phase is not optional.

In one embodiment, the process also comprises:
submitting one or all of the solid/liquid heavy phase (if present) and the phase heavier than the organic phase, partly or in totality, to an extraction step under conditions effective to extract isoprenoid compound from cells and/or host cell debris contained therein, thereby generating one or several streams containing the extracted isoprenoid compound,
optionally:
separating each stream obtained into a solid/liquid light phase stream and a solid/liquid heavy phase stream, or
diluting with water each stream obtained,
adding the salt and the surfactant to the stream(s) generated by the extraction step or to the solid/liquid light phase stream(s) or to the water diluted stream(s).

The invention also provides a process for the production of an isoprenoid compound, comprising the following steps:
(i) providing a micro-organism, optionally genetically engineered, capable of producing the isoprenoid compound;
(ii) fermenting a fermentable medium using said micro-organism; and
(iii) recovering the fermentation product from the fermentation mixture by a process according to the invention.

BRIEF DESCRIPTION OF THE FIGURES

The teaching of the application is illustrated by the following Figures which are to be considered as illustrative only and do not in any way limit the scope of the claims.

DETAILED DESCRIPTION OF THE INVENTION

Figure 1:
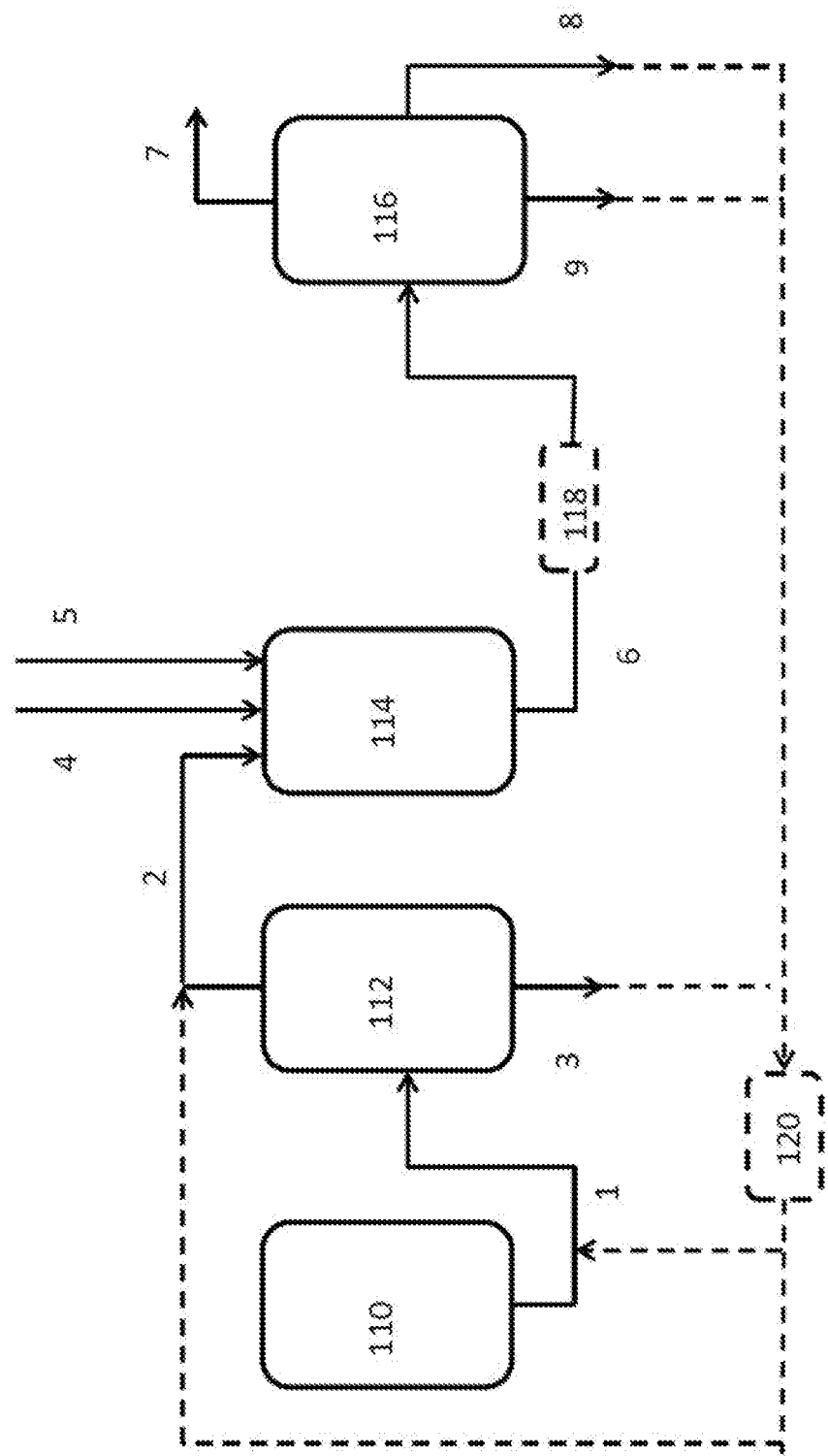
FIG. 1: Schematic representation of a process for the recovery of farnesene from a fermentation mixture according to an embodiment of the method disclosed herein.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. Where reference is made to embodiments as comprising certain elements or steps, this encompasses also embodiments which consist essentially of the recited elements or steps.

The recitation of numerical ranges by endpoints includes all numbers and fractions subsumed within the respective ranges, as well as the recited endpoints.

All documents cited in the present specification are hereby incorporated by reference in their entirety. In particular, the teachings of all documents herein specifically referred to are incorporated by reference.

With "bio-organic compound" or "microbial-derived organic compound" is meant herein an organic compound that is made by microbial cells, including recombinant microbial cells as well as naturally occurring microbial cells.

The term "cell" refers to a microorganism, capable of being grown in a liquid growth medium.

The term "dry weight" or "dry matter" means weight determined in the relative absence of water. For example, reference to cells as comprising a specified percentage of a particular component by dry weight means that the percentage is calculated based on the weight of the cell after substantially all water has been removed (until constant weight).

The term "dry cell weight" or "dry cell matter" or "total suspended solids" means weight determined in the relative absence of water after sample washing for insoluble solids removal.

The term "isoprenoid compound" here refers to compounds capable of being derived from isopentenyl diphosphate (IPP).

The term "microbial cell" refers to organisms such as algae, bacteria, fungi, protest and combinations thereof, e.g. unicellular organisms.

The term "cell-associated" as used herein in connection to fermentation products refers to fermentation products that are associated to the host cell or host cell debris.

The term "emulsion" generally refers to a mixture of two immiscible liquids, such as water and an oil. As used herein, it particularly refers to a mixture of a bio-organic compound envisaged herein and water.

The term "host cell" as used herein refers to a microbial cell which is used for the production of a bio-organic compound. The host cell may be a recombinant cell, which implies that is has been genetically modified to induce or increase the production of the bio-organic compound. In particular embodiments, the host cell contains a foreign DNA and/or has one or more genetic modifications compared to the wildtype organism which affects the production of the bio-organic compound. However, also considered host cells are microbial cells naturally producing a bio-organic compound of interest.

A. Microbial Fermentation

The bio-organic compounds envisaged herein are produced by microbial fermentation. Microbial production of organic compounds is well known in the art, and the invention is applicable to any technique deemed suitable by a skilled person involving microbial fermentation. Typically, micro-organisms are cultured under conditions suitable for the production of the organic compounds by the microbial host cells. Suitable conditions include many parameters, such as temperature ranges, levels of aeration, pH and media composition. Each of these conditions, individually and in combination, is typically optimized to allow the host cell to grow and/or to ensure optimal production of the organic compound of interest. Exemplary culture media include broths or gels. The host cells may be grown in a culture medium comprising a carbon source to be used for growth of the host cell. Exemplary carbon sources include carbohydrates, such as glucose, fructose, cellulose, or the like, that can be directly metabolized by the host cell. In addition, enzymes can be added to the culture medium to facilitate the mobilization (e.g., the depolymerization of starch or cellulose to fermentable sugars) and subsequent metabolism of the carbon source. A culture medium may optionally contain further nutrients as required by the particular microbial strain, including inorganic nitrogen sources such as ammonia or ammonium salts, and the like, and minerals and the like. Other growth conditions, such as temperature, cell density, and the like are generally selected to provide an economical process. Temperatures during each of the growth phase and the production phase may range from above the freezing temperature of the medium to about 50° C. The fermentation may be conducted aerobically, anaerobically, or substantially anaerobically. Briefly, anaerobic conditions refer to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1 oxygen. The percent of oxygen can be maintained by, for example, sparging the culture with an $N_2/CO_2$ mixture or other suitable non-oxygen gas or gasses. The fermentation can be conducted continuously, batch-wise, or some combination thereof. Conventional fermentation bioreactors, shake flasks, test tubes, microtiter dishes, and petri plates can be used.

B. Microbial Cell

Suitable micro-organisms for fermentation are known in the art. Non-limiting examples of suitable micro-organisms include bacteria such as *Escherichia* (e.g. *E. coli*), *Bacillus* or *Lactobacillus* species, fungi, in particular yeasts such as *Saccharomyces* (e.g. *S. cerevisiae*) or *Pichia* species, or algae such as *Chlorella* species. In particular embodiments, the microbial host cell is a fungus, preferably a yeast. The micro-organisms may naturally produce the bio-organic compound of interest, or they may have been genetically modified (i.e. recombinant micro-organisms) to ensure production of the bio-organic compound of interest.

Suitable micro-organisms for use in the present invention are capable to produce an isoprenoid compound; in particular, the micro-organism is capable to excrete an isoprenoid compound.

Non-limiting examples of micro-organisms suitable for the present invention are genetically modified host cells as described in the international applications WO 2013/071172, WO2014/144135, WO2008/039499, WO2007/140339, WO2006/014837, which are incorporated by reference herein.

C. Bio-Organic Compound

The bio-organic compound envisaged therein is an isoprenoid compound, in particular a terpene or polyterpene.

Terpenes are a large class of hydrocarbons that are produced in many organisms. They are derived by linking units of isoprene ($C_5H_8$), and are classified by the number of isoprene units present. Hemiterpenes consist of a single isoprene unit. Isoprene itself is considered the only hemiterpene. Monoterpenes are made of two isoprene units, and have the molecular formula $C_{10}H_{16}$. Examples of monoterpenes are myrcene, geraniol, limonene, and terpineol. Sesquiterpenes are composed of three isoprene units, and have the molecular formula $C_{15}H_{24}$. Examples of sesquiterpenes are farnesene, farnesol, amorpha-4,11-diene and patchoulol. Diterpenes are made of four isoprene units, and have the molecular formula $C_{20}H_{32}$. Examples of diterpenes are cafestol, kahweol, cembrene, and taxadiene. Sesterterpenes are made of five isoprene units, and have the molecular formula $C_{25}H_{40}$. An example of a sesterterpene is geranylfarnesol. Triterpenes consist of six isoprene units, and have the molecular formula $C_{30}H_{48}$. Tetraterpenes contain eight isoprene units, and have the molecular formula $C_{40}H_{64}$. Biologically important tetraterpenes include the acyclic lycopene, the monocyclic gamma-carotene, and the bicyclic alpha- and beta-carotenes. Polyterpenes consist of long chains of many isoprene units. Natural rubber consists of polyisoprene in which the double bonds are cis.

When terpenes are chemically modified (e.g., via oxidation or rearrangement of the carbon skeleton) the resulting compounds are generally referred to as terpenoids, which are also known as isoprenoids.

An isoprenoid compound is typically composed of repeating five-carbon isopentenyl diphosphate (IPP) units, although irregular isoprenoids and polyterpenes have been reported.

In one embodiment, the isoprenoid compound is:

(a) selected from the group consisting of a hemiterpene, monoterpene, sesquiterpene, diterpene, triterpene, tetraterpene, and polyterpene, or (b) an isoprenoid which is not a carotenoid, or (c) a C5-C20 isoprenoid, or (d) selected from the group consisting of abietadiene, amorphadiene, carene, α-farnesene, β-farnesene, farnesol, geraniol, geranylgeraniol, isoprene, linalool, limonene, myrcene, nerolidol, ocimene, patchoulol, β-pinene, sabinene, γ-terpinene, terpinolene and valencene.

In one embodiment, the isoprenoid compound is a C5-C20 isoprenoid, in particular which may not be a carotenoid.

In particular, when the isoprenoid compound is an hemiterpene, it is isoprene.

In particular, when the isoprenoid compound is a monoterpene, it may be selected from carene, geraniol, linalool, limonene, myrcene, ocimene, β-pinene, sabinene, γ-terpinene, terpinolene.

In particular, when the isoprenoid compound is a sesquiterpene, it may be selected from abietadiene, amorphadiene, farnesene (α-farnesene, β-farnesene), farnesol, nerolidol, patchoulol and valencene.

In particular, when the isoprenoid compound is a diterpene, it may be geranylgeraniol. In a particular embodiment, the isoprenoid compound is a sesquiterpene.

In preferred embodiments, the isoprenoid compound is farnesene. In further embodiments, the isoprenoid compound is α-farnesene, β-farnesene or a mixture thereof.

D. Overall Recovery Process

Provided herein are methods for recovering bio-organic compounds, in particular isoprenoic compounds, from a fermentation mixture. A fermentation mixture (also referred to herein as fermentor broth or whole cell broth (WCB)) typically comprises micro-organisms, a culture medium and, once cultivation has started, the fermentation products or bio-organic compounds produced by the micro-organisms. These bio-organic compounds are preferably released or secreted by the micro-organisms in the culture medium as bio-organic compounds, from which they may be recovered.

Typically, the methods of recovery involve separation of the cellular fraction from the rest of the fermentation medium. This is in the art typically ensured by centrifugation, whereby a microbial pellet is generated and discarded, while the organic phase generally supernatant is used for further extraction of the bio-organic compound. Some of the bio-organic compounds of interest will remain at least in part associated to the microbial host cell during the standard recovery processes (referred to herein as cell-associated bio-organic compounds). These are typically lost in current microbial production processes with the microbial pellet.

The fraction of the fermentation medium from which the cellular fraction has been removed may further be treated for recovery of the bio-organic compound using conventional recovery processes including, but not limited to liquid-liquid separation.

Another source of loss of bio-organic compounds is due to emulsion formation, which is inherent to microbial production systems. Indeed, emulsion formation can be promoted in the fermentation medium by the mechanical energy from fermentation (e.g. from agitators or fermentation gases produced by the microbial host cells), or by the microbial host cells or various bio-molecules therein.

Provided herein are recovery processes for bio-organic compounds from a fermentation mixture characterized in that they comprise the recovery of said bio-organic compounds comprised in emulsions, here emulsions of bio-organic compounds in water.

Accordingly, in an aspect, the invention comprises methods for the (improved) recovery of bio-organic compounds from a fermentation mixture, which methods comprise recovering the bio-organic compounds which are present in the fermentation medium in emulsions in presence of a salt and a surfactant.

In particular embodiments, the methods comprise the steps of providing a fermentation mixture comprising micro-organisms, a culture medium and the fermentation products or bio-organic compounds produced by the micro-organisms; performing a solid/liquid separation of the fermentation mixture into a heavy phase and a light phase; and recovering bio-organic compounds comprised in an emulsion from the solid/liquid light phase.

It will however be understood by the skilled person that, while it is of general interest to separate the micro-organisms from the fermentation mixture for the recuperation of the bio-organic compounds, it can be envisaged that the methods of the present invention could also be carried out without separating the micro-organisms from the fermentation medium. More particularly, the methods of the present invention, in particular the methods relating to the recovery of bio-organic compounds contained in an emulsion, may also be considered on the whole fermentation medium or on other fractions of fermentation medium containing cells and/or host cell debris.

Optional Solid/Liquid Separation Step

In particular embodiments, the methods of the invention comprise a solid/liquid separation step. Such separation allows obtaining a fraction of the fermentation medium which will be further submitted to the demulsifying step.

In a preferred embodiment, this step is not optional.

The solid/liquid separation step, which is a widely-established step in the extraction of bio-organic compounds from fermentation medium, separates the micro-organisms from the fermentation mixture. The stream comprising the micro-organisms is also referred to herein as "microbial pellet", or "solid/liquid heavy phase". This stream comprises the micro-organisms and cell-associated bio-organic compounds, and may further comprise host cell debris, culture medium and bio-organic compounds. The solid/liquid heavy phase is preferably a liquid stream. The supernatant or light phase obtained by solid/liquid separation of the fermentation mixture, also referred to herein as "solid/liquid light phase" or "concentrated clarified broth (CCB)", comprises the culture medium, free bio-organic compounds (organic phase) and bio-organic compounds comprised in an emulsion, and may further comprise host cell debris.

The solid/liquid separation of the fermentation mixture may be achieved by well-known techniques, including, without limitation, centrifugation, filtration, and decantation, preferably by centrifugation. A centrifuge can separate the fermentation mixture in batch or on a continuous flow basis. Preferably continuous flow centrifugation is used in the methods described herein. A non-limiting example of a centrifuge suitable for solid/liquid separation of a fermentation mixture as taught herein is a disk stack centrifuge, such as a disk stack centrifuge with nozzles. Centrifugation conditions can be suitably determined by the skilled person to achieve the desired solid/liquid separation.

Demulsifying Step (a)

The present invention provides a new method for recovering isoprenoid compound from an emulsion with reduced amounts of chemicals.

It will be understood that the methods can be performed either on the fermentation medium as such, i.e. comprising the cellular material as well as the non-cellular material, or on a concentrated fraction of the fermentation medium, i.e. comprising a concentrated amount of isoprenoid compound. For instance, the demulsifying step can be performed on a fraction of the fermentation medium which is the solid/liquid light phase of a solid/liquid separation carried out on the fermentation medium.

The methods can also be performed on a fraction of the fermentation medium obtained by extracting isoprenoid compounds from cells and/or debris contained in the fermentation medium and/or in any fraction of the fermentation medium obtained through the overall recovery process.

In some embodiments, the fermentation medium fraction can be a liquid stream obtained by extracting isoprenoid compounds from a solid/liquid heavy phase obtained from a solid/liquid separation of the fermentation medium into a solid/liquid heavy phase and a solid/liquid light phase. Some bio-organic compounds are indeed associated to the cells and/or host cell debris contained in this solid/liquid heavy phase (e.g. located in an inner cell compartment or adsorbed on the cell wall). Extracting those bio-organic compounds from this solid/liquid heavy phase allows recovering an emulsion containing the bio-organic compound from which the isoprenoid compound can be recovered by the methods of the present invention.

In some embodiments, the fermentation medium fraction can be a liquid stream obtained by extracting isoprenoid compounds from a liquid/liquid heavy phase. This liquid/liquid heavy phase is obtained from a liquid/liquid separation of a solid/liquid light phase into a liquid/liquid heavy phase and a liquid/liquid light phase. The solid/liquid light phase is the one obtained as already explained from the optional solid/liquid separation of the fermentation medium into a solid/liquid heavy phase and a solid/liquid light phase. In one embodiment, this liquid/liquid heavy phase can be submitted to a second solid/liquid separation to be separated into a second solid/liquid light phase and a second solid/liquid heavy phase. Isoprenoid compounds are then extracted from the second solid/liquid light phase.

In some embodiments, the fermentation medium fraction can be a liquid stream obtained by extracting isoprenoid compounds from the phase heavier than the organic phase or from the solid phase containing host cell debris and cells obtained in step (b).

In a preferred embodiment, the above fermentation medium fractions are generated by the overall recovering process of the invention including:
- an optional step for separating the fermentation medium into a solid/liquid light phase and a solid/liquid heavy phase,
- a demulsification step in presence of a salt and a surfactant generating an organic phase containing the isoprenoid compound and a phase heavier than the organic phase,
- a step for separating the organic phase containing the isoprenoid compound from the phase heavier than the organic phase.

The above fractions of the fermentation medium and/or the fermentation medium can be submitted to the demulsifying step (a) separately or mixed.

In some embodiments, the fermentation medium or fraction thereof treated in step (a) may comprise up to 35% v/v of cells (living or dead cells) and/or host cell debris.

The % v/v of cells and/or debris can be measured by usual methods such as determination of volume ratios obtained by centrifugation in a capillary tube.

For example, a fermentation medium may contain up to 35% v/v or up to 30% v/v of cells. In general, about 1-5% v/v are cells still containing the isoprenoid compound.

By way of example, a fraction of the fermentation medium which is a light phase of a solid/liquid separation of the fermentation medium may contain up to 6% vol of cells/host cells debris. In general, about 2 to 5% v/v are cells still containing the isoprenoid compound.

By way of example, a fraction of the fermentation medium which is a heavy phase of a solid/liquid separation of the fermentation medium may contain up to 70% v/v of cells/host cells debris. In general, less than 1% v/v are cells still containing the isoprenoid compound.

By way of example, a fraction of the fermentation medium which is a light phase of a liquid/liquid separation of the liquid/solid light phase may contain up to 2% v/v of cells/host cells debris.

By way of example, a fraction of the fermentation medium which is a heavy phase of a liquid/liquid separation of the liquid/solid light phase may contain up to 8% v/v of cells/host cells debris. In general, about 5 to 7% v/v are cells still containing the isoprenoid compound.

This demulsifying step (a) is performed in presence of a salt and a surfactant in the fermentation medium or a fraction thereof to demulsify this composition. Surprisingly, a synergetic effect in the demulsification is observed in the presence of both a salt and a surfactant, since this combination allows either:
- reducing the surfactant concentration at constant bio-organic compound recovery yield by comparison with a system containing only surfactant, or
- increasing the bio-organic compound recovery yield at constant surfactant concentration by comparison with a system containing only surfactant.

This effect can be observed for any of the fermentation medium or fraction thereof treated, at a salt concentration of 0.01 mol/L or more, for example in the salt concentration ranges disclosed below.

The surfactant may be added with the salt or separately, before or after the salt. The surfactant and/or the salt may be added prior or during the demulsifying step (a), eventually prior the optional solid/liquid separation step.

As used herein, a "salt" refers of an ionic compound composed of cations and anions forming a neutral product and without net charge. These ions can be inorganic (chloride $Cl^-$) or organic (acetate $CH_3COOH$) and monoatomic (Fluoride $F^-$) or polyatomic (Sulfate $SO_4^{2-}$).

Salts suitable for use with the present invention include, but are not limited to, alkali metal salts, alkali earth metal salts, or the like, and combinations thereof. Negatively charged ionic species present in a salt for use in the present invention include, but are not limited to, halides, sulfate, bisulfate, sulfite, phosphate, hydrogen phosphate, dihydrogen phosphate, carbonate, bicarbonate, acetate, bromides, bromates, or the like, and combinations thereof.

In some embodiments, a salt for use with the present invention is selected from: sodium chloride, sodium sulfate, sodium carbonate, calcium chloride, potassium sulfate, magnesium sulfate, ammonium sulfate, potassium chloride, iron chloride, iron sulfate, aluminum sulfate, and combinations thereof. In some embodiments, a salt does not include NaOH. In some embodiments, the salt is a salt of a polyvalent cation, such as $Ca^{2+}$, $Mg^{2+}$, $Al^{3+}$, or any other polyvalent cation. The salt can be a chloride, bromide, bromate or any other salt mentioned above. In some embodiment, the salt is an alkali earth metal salt.

Without wishing to be bound by a theory, as the surface of the drops in the emulsion is negatively charged, the stability of the drops may be governed by the charge of the counter-ions and polycations such as $Ca^{2+}$, $Mg^{2+}$, $Al^{3+}$, may improve the demulsifying.

A salt can be introduced into the fermentation medium or fraction thereof as a solid (e.g., in crystalline, amorphous, pelletized, and/or granulated form), and/or as a solution (e.g., a dilute solution, a saturated solution, or a supersaturated solution) containing, for example, water, an alcohol, and the like, and combinations thereof.

In some embodiments, the concentration of salt present in the fermentation medium or the fraction thereof in the demulsifying step is from 0.01 mol/L to 5 mol/L, or from 0.05 to 4.5 mol/L, or from 0.05 mol/L to 4 mol/L, or from 0.05 to 3 mol/L, or from 0.05 to 2 mol/L, or from 0.05 to 1 mol/L, or any combination of these ranges. In a preferred embodiment, this salt concentration is from 0.01 mol/L to 0.5 mol/L or from 0.05 mol/L to 0.5 mol/L or from 0.05 mol/L to 0.25 mol/L or from 0.05 mol/L to 0.15 mol/L, or any combination of these ranges.

The term "surfactant" refers to a compound that reduces the surface tension (or interfacial tension) between two liquids or between a liquid and a solid.

Surfactants are usually organic compounds that are amphiphilic, which means they contain both hydrophobic groups and hydrophilic groups.

Anionic surfactants contain anionic functional groups, such as sulfate, sulfonate, phosphate, and carboxylates.

Suitable surfactants to use in the present invention include, but are not limited to, non-ionic surfactants, anionic surfactants and combination thereof, in particular anionic surfactants which are water soluble.

In some embodiments, anionic surfactants are soluble in water.

Anionic surfactants which may be utilized include sulfates and sulfonates, sodium dodecylsulfate (SDS), sodium dodecylbenzene sulfonate, sodium dodecylnaphthalene sulfate, dialkyl benzenealkyl sulfates and sulfonates, acids such as abitic acid, combinations thereof. Other suitable anionic surfactants include, alkyldiphenyloxide disulfonate including two C6-C16 hydrocarbonchains branched on each of the sulfonated aromatic rings, such as, by example, DOW-FAX™ 2A1 from Dow Chemical Company.

In a preferred embodiment, the surfactant is a sulfonate, in particular a disulfonate. Advantageously, this surfactant is soluble in water.

Examples of non-ionic surfactants that may be utilized for the process illustrated herein include, for example, polyether polyols, in particular copolymers of propylene oxide (PO) and ethylene oxide (EO), including those made by capping polypropylene glycols with ethylene oxide, as those available from The Dow Chemical Company as TERGITOL™ L.

In one embodiment, the non-ionic surfactant is a polyether glycol having a molecular weight of at least 2400 g/mol. In Particular, the molecular weight is less than 3000 g/mol, preferably less than 2800 g/mol. The molecular weight may have a value within a range defined by any combination of these limits.

In a preferred embodiment, the non-ionic surfactant is a polyether glycol having a molecular weight of at least 2400 g/mol. Advantageously, this surfactant is soluble in water.

Combinations of these surfactants and any of the foregoing surfactants may be utilized in embodiments.

The presence of a salt or a mixture of salts, at any of the above mentioned salt concentrations, allows demulsification using surfactant concentrations from $5 \cdot 10^{-3}$ to 1% v/v or from 0.01 to 0.5% v/v, or from 0.01 to 0.2% v/v, or from 0.01 to 0.15% v/v, or any combination of these ranges.

In some embodiments, a surfactant concentration from $5 \cdot 10^{-3}$ to 1% v/v and a salt concentration from 0.01 mol/L to 5 mol/L, or from 0.05 mol/L to 4.5 mol/L, or from 0.1 mol/L to 4 mol/L, or from 0.5 to 3 mol/L. are combined with the optional heating step described below. Such combination is particularly advantageous when the surfactant is a non-ionic surfactant, in particular a non-ionic surfactant comprising a poly-EO or poly-EO polar head. In a preferred embodiment, the non-ionic surfactant is a polyether polyol.

In some embodiments, a surfactant concentration from $5 \cdot 10^{-3}$ to 0.2% v/v, or from $5 \cdot 10^{-3}$ to 0.15% v/v, and a salt concentration from 0.01 mol/L to 0.5 mol/L or from 0.05 mol/L to 0.5 mol/L are particularly advantageous when the surfactant is an anionic surfactant, in particular a water-soluble surfactant, as any of those listed above. In a preferred embodiment, the anionic surfactant is a sulfonate, more preferably a disulfonate.

A surfactant can be introduced as a solid (e.g., in crystalline, amorphous, pelletized, and/or granulated form), and/or as a solution (e.g., a dilute solution, a saturated solution, or a super-saturated solution) containing, for example, water, an alcohol, and the like, and combinations thereof.

Demulsifying step (a) is preferably performed without altering the pH of the fermentation medium or fraction thereof. In particular, no addition of acid or base is needed, during or prior step (a). In a preferred embodiment, the pH of the fermentation medium or the fraction thereof is in the range from 2 to 7.

Advantageously, the fermentation medium or fraction thereof is stirred after addition of salt and/or surfactant (and before separating step (b)) for homogenization purpose. Such stirring may last at least 30 s, or 1 min, or 5 min or 15 min or 30 min, and/or may last at most 24 hours, or 15 hours or 12 hours. Such stirring may be performed with duration ranges defined by any combination of these limits.

Advantageously, demulsifying step (a) is performed at ambient temperature, without heating or cooling the fermentation medium or fraction thereof. In particular, there is no need to monitor a temperature above or below a phase inversion temperature or cloud point At the end of the demulsification step (a), a stream having a organic phase containing the isoprenoid compound and a phase heavier than the organic phase is obtained, and optionally a solid phase containing host cell debris and cells.

This stream may contain more particularly: an oil organic phase also referred therein as "organic phase" containing the isoprenoid compound, eventually a residual emulsion phase, a heavy phase also referred therein as the "phase heavier than the organic phase" containing mainly water, and eventually, at the bottom, deposits (debris if any and dead cells).

Optional Heating Step

In some embodiments, the separation step (b) is preceded by a heating step in which the fermentation medium or the fraction thereof treated in step (a) is heated to improve the oil recovery. In a preferred embodiment, the heating is performed after addition of the surfactant.

The heating temperature is chosen inferior to a temperature at which the isoprenoid compounds are degraded or decomposed. The isoprenoid compound is said to be degraded when dimerization and/or oligomerization occur. The isoprenoid compound is decomposed when its structural carbon chain is broken.

The heating temperature can be from 40 to 120° C., or from 40 to 90° C., or from 50 to 80° C., or from 50 to 80° C. Advantageously, this heating step may be performed for a period of less than a few minutes at the higher temperature to avoid formation of by-products such as dimers or oligomers. An appropriate heating duration may be determined by analysis of the evolution of isoprenoid compounds as a function of time and temperature. For example, the kinetic of dimerization or oligomerization of the isoprenoid compound can be analysed as a function of time and temperature.

In some embodiments, the stream obtained in step (a) is heated at the above-mentioned temperatures.

This heating step is particularly advantageous when using a non-ionic surfactant.

This heating can be performed by passing the stream in a heat exchanger.

Separation Step (b)

This step allows separation of the organic phase obtained in step (a).

In some embodiments, the organic phase containing the isoprenoid compound is separated by a liquid-liquid separation, such as centrifugation.

The liquid/liquid separation step, which is a widely-established step in the extraction of bio-organic compounds, separates the bio-organic compound from the phase heavier than the organic phase. The light phase obtained comprising the bio-organic compound is also referred to herein as "crude", "organic phase" or "liquid/liquid light phase". This stream comprises the bio-organic compounds produced by the fermentation and may further comprise some cells, generally dead cells. The heavy phase recovered, also referred to herein as "phase heavier than the organic phase" or "liquid/liquid heavy phase", comprises the culture medium, cells and may further comprise host-cell debris, free bio-organic compounds and bio-organic compounds comprised in an emulsion. A further solid phase may be obtained, also referred to herein as "discharged phase", "discharge composition" which comprises the culture medium, host-cell debris, cells and may further comprise free bio-organic compounds and bio-organic compounds comprised in an emulsion.

The liquid/liquid separation may be achieved by well-known techniques, including, without limitation, centrifugation, filtration, and decantation, preferably centrifugation.

A centrifuge can separate liquid/liquid light phase in batch or on a continuous flow basis. Preferably continuous flow centrifugation is used in the methods described herein. A non-limiting example of a centrifuge suitable for liquid/liquid separation of a fermentation mixture as taught herein is a disk stackcentrifuge. Centrifugation conditions can be suitably determined by the skilled person to achieve the desired liquid/liquid separation.

Optional Extraction of Isoprenoid Compounds Associated in Cells

The phase heavier than the organic phase or the solid phase containing host cell debris and cells obtained in step (b), the solid/liquid heavy phase or the liquid/liquid heavy phase previously mentioned all contain cells (dead or living cells depending on the fraction) and/or host cell debris, which all contains some isoprenoid compounds.

In some embodiments, the isoprenoid compounds contained in cells and/or host cell debris of one or several of these phases are extracted and a liquid stream containing the isoprenoid compounds is obtained. Such liquid stream is then further submitted to the demulsifying step (a), optionally after a solid/liquid separation (in general the same as the previously mentioned solid/liquid separation) or after a water dilution step in which the liquid stream containing the isoprenoid compounds is diluted with water.

The dilution of the liquid stream containing the isoprenoid compounds with water may be from 1/0.5 to 0.5/1, preferably from 1/0.8 to 0.8/1, most preferably from 1/0.9 to 0.9/1, for example 1/1.

This extraction can be obtained by any appropriate techniques known in the art to extract/release a bio-organic compound from a cell and/or host cell debris. These techniques include, but are not limited to, mechanically treating, chemically treating, enzymatically treating, physically treating, or combinations thereof.

As used herein, mechanically treating includes, but is not limited to, homogenizing a cell, applying ultrasound to a cell, cold-pressing a cell, milling a cell or the like, and combinations thereof. In a preferred embodiment, milling is used to extract the bio-organic compound from the cells and/or host cell debris.

Mechanically treating a cell can include, but is not limited to, processes utilizing a French pressure cell press, a sonicator, a homogenizer, a ball mill, a rod mill, a pebble mill, a bead mill, a high pressure grinding roll, a vertical shaft impactor, an industrial blender, a high shear mixer, a paddle mixer, a polytron homogenizer or the like, and combinations thereof.

As used herein, physically treating can include, but is not limited to, heating a cell, decompression, osmotic shock. Heating a cell can include, but is not limited to, resistive heating, convection heating, steam heating, heating in a fluid bath, heating with solar energy, heating with focused solar energy, and the like, any of which can be performed in a tank, pool, tube, conduit, flask, or other containment device.

As used herein, chemically treating includes, but is not limited to contacting a cell with a chemical, such as antibiotics, chelating agents, solvents, detergents, chaotropes.

Enzymatic lysing refers to lysis of a cell wall or cell membrane of a cell by contacting the cell with one or more enzymes. Enzymatic methods include lytic enzymes or autolysis.

The invention will be further understood with reference to the following non-limiting examples.

EXAMPLES

Example 1: Description of the Process According to an Embodiment

FIG. 1 shows a schematic representation of a process for the recovery of farnesene from a fermentation mixture according to an embodiment of the present invention. A fermentation mixture (whole cell broth, stream #1) prepared in a bioreactor 110 is fed into in a solid/liquid separation device 112, here a centrifuge, such as a disk stack centrifuge with nozzles, where it is separated in a light phase (solid/liquid light phase stream #2) and a heavy phase (solid/liquid heavy phase, streams #3).

As well known by the man skilled in the art, it should be noted that if storage for several days of the WCB is envisaged, it is possible to add a solvent to prevent or delay the build-up of cell-associated fene that occurs. This solvent, also called overlay, may be added to the fermentation medium during fermentation or right after harvest to recover WCB. In case of overlay, the organic phase contained in the fermentation medium may therefore not be the supernatant phase depending on the solvent used.

The solid/liquid light phase (concentrated cell broth, stream #2) is composed of free farnesene, water, water soluble species, including emulsions comprising farnesene, and some yeasts. This solid/liquid light phase stream #2 is fed into a tank 114 for demulsification. To this effect, a salt (stream #4) and a surfactant (stream #5) are introduced into the tank 114. A stream #6 is generated containing an organic phase containing the isoprenoid compound and a phase heavier than the organic phase.

The stream #6 exiting the demulsificating tank 114 is fed into a liquid/liquid separation device 116, here a centrifuge, such as a disk stack centrifuge, where it is separated in a light phase (liquid/liquid light phase stream #7) and a phase heavier than the organic phase. This phase heavier than the organic phase comprises a heavy phase (liquid/liquid heavy phase, stream #8) and a solid phase (stream #9). The heavy phase (stream #8) is an aqueous phase.

The light phase (crude containing most of the farnesene, stream #7) can be further treated. It can for example be submitted to a polishing centrifuge to remove some dead cells and dissolved lipids. The farnesene stream obtained may then be purified by appropriate treatments such as evaporation followed by a hydrogenation step and then a distillation step. These treatments are usual and not described herein.

Optionally, the stream #6 exiting the demulsificating tank 114 can be heated, for example by passing through a heat exchanger 118, before the separation in the separation device 116. This may allow better separation of the organic phase (stream #7).

The heavy solid/liquid phase (stream #3), comprises yeasts, aqueous phase as well as dead cells, a residual emulsion and some free farnesene.

The heavy phase (liquid/liquid heavy phase, stream #8) contains mainly an aqueous phase but also some yeasts, dead cells as well as a residual emulsion and some free farnesene.

The solid phase (stream #9) also contains yeasts, aqueous phase as well as dead cells, a residual emulsion and some free farnesene.

In a particular embodiment of the invention, some or all of the above streams (#3, #8, #9) containing yeasts/dead cells/cells debris may be recycled, partly or in totality, into the solid/liquid separation device 112 or into the demulsification tank 114. Preferably, before entering the separation device 112 or the demulsification tank 114, the recycled streams pass through a disrupting device 120 under conditions efficient to release the farnesene trapped into the yeasts/dead cells/cells debris into the solution. This disrupting can for example be performed by milling, for example in a bead mill. The solution obtained contains an emulsion (farnesene in water) which can be broken in the demulsification tank 114 directly, or preferably after a water dilution (not represented) or after passing through the solid/liquid separation device 112.

It should be noted that the stream #2 may be further submitted to a liquid/liquid separation (not represented) to obtain a liquid/liquid light phase sent to demulsification tank 114 and a liquid/liquid heavy phase sent to the disrupting device 112 and further demulsified in tank 114, optionally after water dilution or solid/liquid separation.

Tests have been performed using a process as the one disclosed into FIG. 1, without recycling streams #3, #8, #9. These tests are developed in examples 2-10.

Oil recovery yield (v/v) is calculated as the ratio between oil volume (mL) and total solution volume in the sample (mL), including the added volume in salt and/or surfactant. Total solution volume is obtained by assuming that the solution accounts for all the dry matter of the emulsion present in the sample, even when the emulsion contains debris. Real yields are therefore higher than calculated yields.

Microbial Cell Composition Tested in Examples 2-10:

A broth containing *Saccharomyces Cerevisiae* cells has been prepared in a fermentor.

The fermentation is run at 30° C. and pH 5, with air flow 100 LPM (Liter per minute) at 15 psi (0.1 MPa) pressure and cane syrup as feedstock.

The total run time of the fermentation is twenty days. In the first 7 days, small volumes of fermentation broths have been prepared in a 250 mL flask before their introduction into the fermentor.

The cells used are genetically modified cells, which produces β-farnesene ($C_{15}H_{24}$, IUPAC name: (6E)-7,11-dimethyl-3-methylidenedodeca-1,6,10-triene). The β-farnesene production is around 150 g/kg.

The broth prepared contains 54% vol of an aqueous phase, 13% vol of emulsion, 30% vol of yeasts, the remaining percents comprise free farnesene and dead cells.

These phases are observed in the following order from the lightest to the heaviest phases after centrifugation:
free farnesene (continuous organic phase),
emulsion (farnesene in water emulsion),
dead cells,
aqueous phase (which may contains some organic droplets),
yeasts.

Four batches have been retrieved at regular intervals from the fermentor.

The tests have been performed on the last batch (4th) retrieved, at the end of the fermentation process, for which the emulsion is usually the most stable.

This 4th batch has been submitted to a concentration by centrifugation (solid/liquid separation) in the following conditions using an Alfa-Laval DX203 centrifuge (a disk stack nozzle centrifuge):
Initial Pump Speed (%): 75
Feed Flowrate calculated (LPM): 3.4
Light Split Ratio (Product/Aq): 80/20
Nozzle size (mm) 0.8
Number of Nozzles: 3

A concentrated cell composition CC1 is obtained containing 43% vol of an aqueous phase, 50% vol of emulsion, 3.4% vol of dead cells, 2.1% vol of free farnesene, the remaining percents comprise yeasts. The order of these phases after centrifugation (from the lightest to the heaviest phases) is the same as the one described for the broth.

Example 2—Effect of pH

The pH is measured with an apparatus WTW series inoLab 720. The initial pH of the CC1 composition is 5.2. The following tests have been performed:
For testing pH>pHinitial: a solution of NaOH (pH=12.8) is introduced continuously into 50 mL of CC1. 10 mL are collected at each unit of pH attained,
For testing pH<pHinitial: a solution of HCl (pH=1.05) is introduced continuously into 50 mL of CC1. 10 mL are collected for each unit of pH attained.

Each 10 mL sampling is centrifuged at 4600 g (g being the earth gravity constant) for 5 minutes using a Rotanta 460 RF Hettich centrifuge to perform a liquid/liquid separation.

The control test corresponds to the CC1 sample centrifuged (pH=5.2), without any pH variation resulting from addition of a base or acid (without addition of NaOH or HCl).

The volume proportions of the oil phase containing free farnesene, the emulsion and the aqueous phase are reported in table 1. The maximum recovery of the oil phase is obtained for the pH 4, 5, 6, close to the initial pH for CC1.

TABLE 1

| pH | % vol oil phase | % vol Emulsion | % vol Aq. phase |
|---|---|---|---|
| 2 | 6 | 14 | 80 |
| 3 | 12 | 14 | 74 |
| 4 | 15 | 14 | 71 |
| 5 | 16 | 17 | 67 |
| 6 | 15 | 15 | 70 |
| 7 | 10 | 15 | 75 |
| 8 | 14 | 13 | 73 |
| 9 | 10 | 15 | 75 |
| 10 | 10 | 12 | 78 |
| Control | 14 | 16 | 70 |

Effects of Surfactants

The following surfactants have been tested in examples 3-10:

TA1: Sorbitan monoleate, a non ionic surfactant commercialized under the name Span® 80, formula:

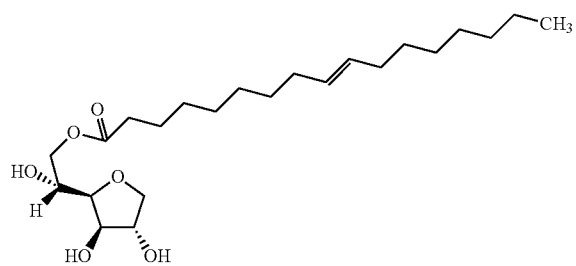 [SMILES: CCCCCCC/C=C/CCCCCCCC(=O)OC[C@@H](O)[C@H]1OC[C@H](O)[C@H]1O]

TA1 is a oil-soluble surfactant, it dissolves in organic solvents including ethanol, toluene and xylene. TA1 is dispersible in water.

TA2 is a polyether polyol (non-ionic surfactant) with a molecular weight of 2500 g/mol, commercialized under the name TERGITOL™ L-62. TA2 has a large hydrophobic section surrounded by two hydrophilic sections. TA2 is soluble in water and soluble in organic solvents, including ethanol, polyethylene glycol, toluene and xylene.

TA3: Alkyldiphenyloxide disulfonate, anionic surfactant, commercialized under the name of DOWFAX™-2A1. This compound comprises two sulfonated aromatic rings linked by an ether function. Two C6 to C16 hydrocarbon chains are branched on these aromatic rings. At least 20% of the chains are C16 chains. TA3 is a hydrosoluble (water soluble) surfactant. TA3 is highly soluble in strong acid and alkali solutions.

Example 3—Effect of Surfactant TA1

100 μL of a mixture of 80/20 (v/v) TA1/isooctane are added to 10 mL of CC1 to obtain a concentration in TA1 of 1% v/v.

The sample is stirred with an ultra-Turrax mixer during 5 min at 9500 rpm and then centrifuged at 4600 g for 5 minutes using a Rotanta 460 RF Hettich centrifuge to perform a liquid/liquid separation. One sample has been further heated at 70° C. in a water bath before centrifugation.

The volume proportions of oil phase containing farnesene, the emulsion and the aqueous phase are reported in table 2. Addition of TA1 does not increase significantly the oil phase proportion, even after heating.

TABLE 2

| Sample | % vol oil phase | % vol Emulsion | % vol Aq. phase |
|---|---|---|---|
| CC1 | 10 | 27 | 63 |
| CC1 + heating at 70° C. | 11 | 18 | 71 |
| CC1 + 1% TA1 | 10 | 26 | 64 |
| CC1 + 1% TA1 + heating at 70° C. | 12 | 15 | 73 |

Example 4—Effect of Surfactant TA2

90 μL of TA2 are added to 30 mL of CC1 to obtain 0.3% v/v of TA2. The mixture is vortexed 30 s and then centrifuged at 4600 g for 5 min. 50 μL of TA2 are added to 10 mL of CC1 to obtain 0.5% v/v of TA2. The mixture is vortexed 30 s and then centrifuged at 4600 g for 5 min.

TABLE 3

| Sample | % vol oil phase | % vol Emulsion | % vol Aq. phase |
|---|---|---|---|
| CC1 | 10 | 27 | 63 |
| CC1 + heating at 70° C. | 11 | 18 | 71 |
| CC1 + 0.3% TA2 | 13 | 15 | 72 |
| CC1 + 0.3% TA2 + heating at 70° C. | 20 | 15 | 65 |
| CC1 + 0.5% TA2 | 14 | 20 | 66 |
| CC1 + 0.5% TA2 + heating at 70° C. | 19 | 14 | 67 |

The centrifugation is performed using a Rotanta 460 RF Hettich centrifuge to perform a liquid/liquid separation. One sample of each concentration has been further heated at 70° C. in a water bath before centrifugation.

The volume proportions of the oil phase containing farnesene, the emulsion and the aqueous phase are reported in table 3. A slight increase of the oil proportion recovered can be observed when the surfactant concentration increases from 0.3 to 0.5% v/v. Heating allows increasing the proportion of oil recovered.

Example 5—Effect of Surfactant TA3

100 μL of TA3 are added to 10 mL of CC1 to obtain 1% v/v of TA3. The mixture is vortexed 30 s and then centrifuged at 4600 g for 5 min using an Rotanta 460 RF Hettich centrifuge to perform a liquid/liquid separation.

The volume proportions of the oil phase containing farnesene, the emulsion and the aqueous phase are reported in table 4. Important proportions of oil can be obtained with TA3 at concentration ranging from 0.25 to 1% v/v.

TABLE 4

| Sample | % vol oil phase | % vol Emulsion | % vol Aq. phase |
|---|---|---|---|
| CC1 | 12 | 23 | 65 |
| CC1 + 0.01% TA3 | 18 | 14 | 68 |
| CC1 + 0.05% TA3 | 18 | 12 | 70 |
| CC1 + 0.10% TA3 | 20 | 11 | 69 |
| CC1 + 0.25% TA3 | 25 | 7 | 68 |
| CC1 + 0.50% TA3 | 25 | 7 | 68 |
| CC1 + 0.75% TA3 | 25 | 8 | 67 |
| CC1 + 1.00% TA3 | 24 | 8 | 68 |

Example 6—Effect of Surfactant TA3+NaCl

Solutions containing 0.1 mol/L (0.1M) NaCl have been prepared as described below. 41 mg of NaCl have been added to 10 mL samples of CC1 containing respectively 0, 0.1, 0.25, 0.5, 0.75, 1% v/v of TA3. Each sample is then vortexed for 30 s and let at ambient temperature 5 minutes. Each sample is then centrifuged at 4600 g for 5 min using an Rotanta 460 RF Hettich centrifuge to perform a liquid/liquid separation.

The volume proportions of the oil phase containing farnesene, the emulsion and the aqueous phase are reported in table 5. No significant change is observed for TA3 concentrations varying from 0.25 to 1% v/v. An increase can be observed for a concentration of TA3 of 0.1% v/v. It should also be noted that addition of NaCl alone (without TA3) tends to stabilize the emulsion as about 5% less oil is recovered, as compared with the control system (CC1 without TA3 and NaCl).

TABLE 5

| Sample | % vol oil phase | % vol Emulsion | % vol Aq. phase |
|---|---|---|---|
| CC1 | 12 | 23 | 65 |
| CC1 + 0.1M NaCl | 7 | 26 | 67 |
| CC1 + 0.1% TA3 + 0.1M NaCl | 22 | 12 | 66 |
| CC1 + 0.25% TA3 + 0.1M NaCl | 25 | 7 | 68 |
| CC1 + 0.5% TA3 + 0.1M NaCl | 25 | 7 | 68 |
| CC1 + 0.75% TA3 + 0.1M NaCl | 25 | 8 | 67 |
| CC1 + 1% TA3 + 0.1M NaCl | 25 | 6 | 69 |

Example 7—Effect of Surfactant TA3+CaCl$_2$)

Solutions containing 0.1 mol/L of CaCl$_2$) have been prepared. 136 mg of CaCl$_2$) have been added to 10 mL samples of CC1 containing respectively 0, 0.05, 0.1, 0.25, 0.5, 0.75, 1% v/v of TA3. The sample is then vortexed for 30 s and let at ambient temperature 5 minutes. The sample is then centrifuged at 4600 g for 5 min using an Rotanta 460 RF Hettich centrifuge to perform a liquid/liquid separation.

The volume proportions of the oil phase containing farnesene, the emulsion and the aqueous phase are reported in table 6. No significant change is observed for TA3 concentrations varying from 0.25 to 1% v/v. An increase can be observed for concentrations of TA3 of 0.05% v/v and 0.1% v/v.

The addition of $CaCl_2$ alone (without TA3) tends to stabilize the emulsion since almost no oil is recovered, as compared with the control system (CC1 without TA3 and $CaCl_2$)).

TABLE 6

| Sample | % vol oil phase | % vol Emulsion | % vol Aq. phase |
|---|---|---|---|
| CC1 | 12 | 23 | 65 |
| CC1 + 0.1M $CaCl_2$ | 1 | 34 | 65 |
| CC1 + 0.05% TA3 + 0.1M $CaCl_2$ | 22 | 10 | 68 |
| CC1 + 0.1% TA3 + 0.1M $CaCl_2$ | 25 | 7 | 68 |
| CC1 + 0.25% TA3 + 0.1M $CaCl_2$ | 25 | 7 | 68 |
| CC1 + 0.5% TA3 + 0.1M $CaCl_2$ | 25 | 8 | 67 |
| CC1 + 0.75% TA3 + 0.1M $CaCl_2$ | 24 | 8 | 68 |
| CC1 + 1% TA3 + 0.1M $CaCl_2$ | 25 | 6 | 69 |

Example 8—Effect of Surfactant TA3+$CaCl_2$)

$CaCl_2$) has been added to CC1 samples to obtain concentration in $CaCl_2$) of 0.1, 0.2, 0.3 and 0.4 mol/L. The CC1 samples contained 0.01% v/v of surfactant. Tests have also been performed with $CaCl_2$) at 0.1, 0.2 and 0.3 mol/L, and 0.05% v/v of surfactant.

The volume proportions of the oil phase containing farnesene, the emulsion and the aqueous phase are reported in table 7. The values obtained in example 7 for and 0.1% v/v of surfactant and 0.1M of $CaCl_2$) are also reported for comparison.

An increase in the oil yield is observed as the $CaCl_2$) concentration varies from 0.1 mol/L to 0.3 mol/L, at 0.05% v/v of TA3. Interestingly for 0.05% v/v of TA3+0.3 mol/l $CaCl_2$), the same oil proportion is recovered as with 0.25 to 1% v/v of TA3 alone (see table 4)

An improvement of the oil yield is also observed as the $CaCl_2$ concentration increases from 0.2 to 0.4 mol/L, at 0.01% v/v of TA3.

TABLE 7

| Sample | % vol oil phase | % vol Emulsion | % vol Aq. phase |
|---|---|---|---|
| CC1 | 12 | 23 | 65 |
| CC1 + 0.1M $CaCl_2$ | 1 | 34 | 65 |
| CC1 + 0.01% TA3 | 18 | 14 | 68 |
| CC1 + 0.01% TA3 + 0.1M $CaCl_2$ | 25 | 7 | 68 |
| CC1 + 0.01% TA3 + 0.2M $CaCl_2$ | 20 | 10 | 70 |
| CC1 + 0.01% TA3 + | 20 | 11 | 69 |

TABLE 7-continued

| Sample | % vol oil phase | % vol Emulsion | % vol Aq. phase |
|---|---|---|---|
| 0.3M $CaCl_2$ | | | |
| CC1 + 0.01% TA3 + 0.4M $CaCl_2$ | 22 | 10 | 68 |
| CC1 + 0.05% TA3 + 0.1M $CaCl_2$ | 22 | 10 | 68 |
| CC1 + 0.05% TA3 + 0.2M $CaCl_2$ | 23 | 9 | 68 |
| CC1 + 0.05% TA3 + 0.3M $CaCl_2$ | 25 | 5 | 70 |
| CC1 + 0.1% TA3 + 0.1M $CaCl_2$ | 25 | 7 | 68 |

Example 9—Effect of Surfactants TA2, TA3

Protocol used for testing salts and surfactants on concentrated cell composition CC1

The following protocol has been used for each test:
Introduction of the appropriate amount of surfactant and/or salt in a centrifuge tube,
Addition of CC1 to bring the final volume to 10 mL, followed by vortex mixing,
Immersion of the tube into a water bath for 30 min, at 60° C.,
Centrifugation of the tubes at 10 000 g for 5 min at 40° C. using a centrifuge Rotanta 460RF Hettich.

The volumes of the phases recovered are reported in table 8. The cream volume is the volume of farnesene in water emulsion.

The control sample (test 1—without surfactant) gives a yield of 28% v/v. The addition of TA2 from 0.1 to 1% v/v slightly increases this yield (5% v/v increment). The yields are similar for the 3 samples containing TA2. The addition of TA3 provides better yields compared to the control sample for concentrations varying from 0.5 to 1% v/v. Results are similar for both surfactants.

TABLE 8 effects of surfactants

| Test | Surfactant | Conc. of surfactant (% v/v) | Cream (mL) | Heavy phase (mL) | Clear Farnesene (mL) | Yield Clear Far./CC1 (% v/v) |
|---|---|---|---|---|---|---|
| 1 | — | 0 | 1.4 | 5.8 | 2.8 | 28 |
| 2 | TA3 | 0.1 | 2 | 5.6 | 2.4 | 24 |
| 3 | TA3 | 0.5 | 1 | 5.5 | 3.5 | 37 |
| 4 | TA3 | 1 | 0.9 | 5.4 | 3.5 | 39 |
| 5 | TA2 | 0.1 | 0.8 | 5.95 | 3.25 | 33 |
| 6 | TA2 | 0.5 | 0.55 | 5.95 | 3.5 | 37 |
| 7 | TA2 | 1 | 1 | 5.8 | 3.2 | 36 |

Example 10—Effect of Surfactants TA2 or TA3 and $CaCl_2$) Salt

The same protocol as in example 9 has been used.
The concentration in surfactants tested were: 0.05% v/v, 0.1% v/v, 0.5% v/v and 1 v/v. $CaCl_2$) was added to obtain $CaCl_2$) concentrations of 0.05M, 0.1M and 0.5M, respectively (5.5 g/L, 11.1 g/L and 55.5 g/l, respectively).

Figure 2:
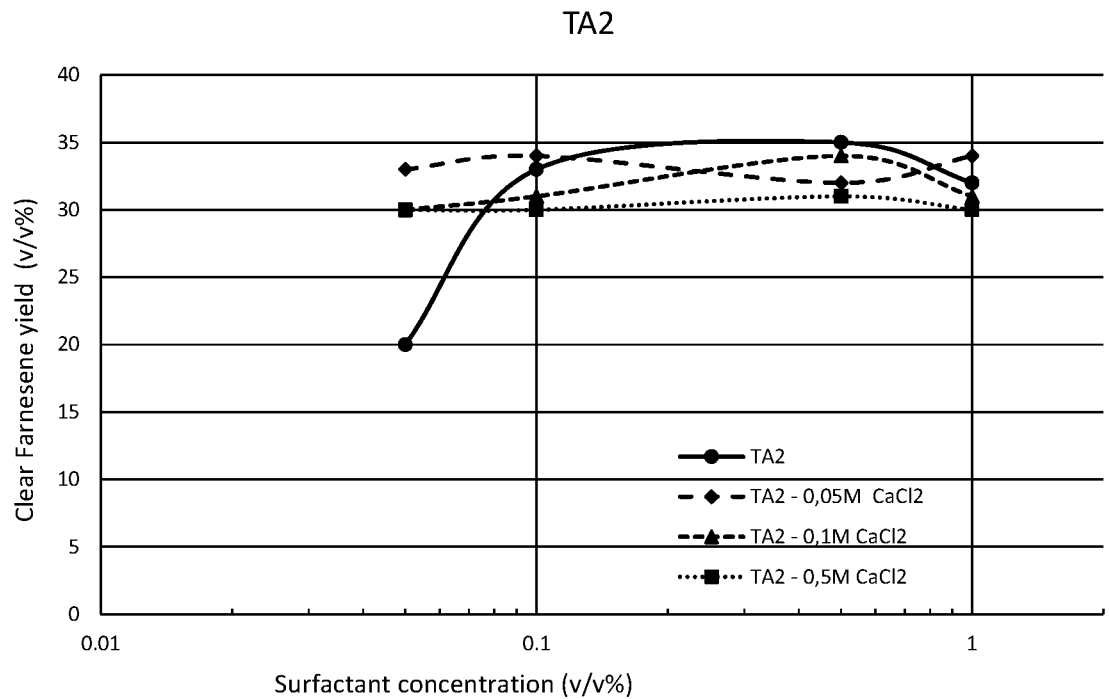
FIG. 2: diagram representing the clear farnesene yield (%) as a function of the concentration of surfactant TA2.
Figure 3:
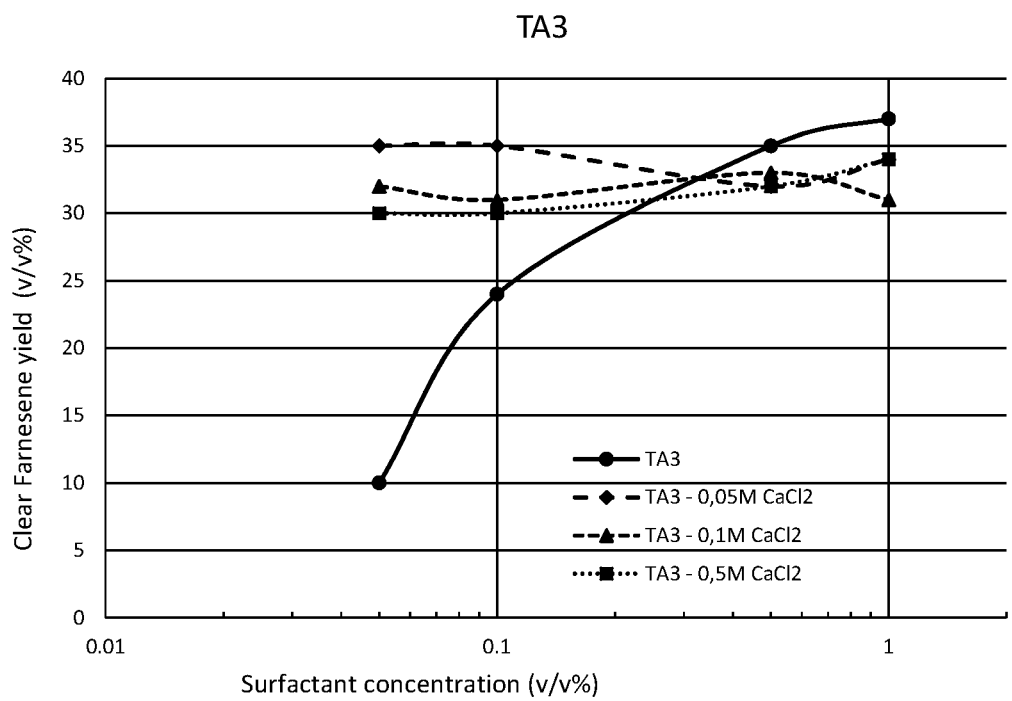
FIG. 3: diagram representing the clear farnesene yield (%) as a function of the concentration of surfactant TA3.

The results are shown on FIG. 2 for TA2 alone and TA2+$CaCl_2$) and on FIG. 3 for TA3 alone and TA3+$CaCl_2$).

The addition of 0.05M $CaCl_2$) provides the best yield for both surfactants. Moreover, the addition of $CaCl_2$) widens the range of surfactant concentration that gives the best yields:

From [0.1;1] % v/v to [0.05;1] % v/v for TA2
From [0.5;1] % v/v to [0.05;1] % v/v for TA3

The surfactant concentration can be reduced by a factor of 2-10 without reducing the oil yield.

The invention claimed is:

1. A process for recovering an isoprenoid compound produced by fermentation from a fermentation medium comprising:
    (a) demulsifying the fermentation medium or a fraction thereof in presence of a salt and a surfactant by addition of the salt and surfactant, the salt being at a concentration of 0.01 mol/L or more, thereby generating a stream having an organic phase containing the isoprenoid compound and a phase heavier than the organic phase, and
    (b) separating the stream obtained in step (a) into the organic phase containing the isoprenoid compound, the phase heavier than the organic phase, and optionally a solid phase containing host cell debris and cells.

2. The process according to claim 1, wherein the fraction of the fermentation medium submitted to step (a) is chosen from:
    a solid/liquid light phase obtained from a solid/liquid separation of the fermentation medium into a solid/liquid heavy phase and a solid/liquid light phase,
    a liquid stream obtained by extracting isoprenoid compounds from a solid/liquid heavy phase obtained from a solid/liquid separation of the fermentation medium into a solid/liquid heavy phase and a solid/liquid light phase,
    a liquid stream obtained by extracting isoprenoid compounds from a liquid/liquid heavy phase itself obtained from a liquid/liquid separation of a solid/liquid light phase into a liquid/liquid heavy phase and a liquid/liquid light phase, said solid/liquid light phase being obtained from a solid/liquid separation of the fermentation medium into a solid/liquid heavy phase and a solid/liquid light phase,
    a liquid stream obtained by extracting isoprenoid compounds from the phase heavier than the organic phase or from the solid phase containing host cell debris and cells obtained in step (b).

3. The process according to claim 1, wherein at least one of the liquid streams obtained by extraction is submitted to a solid/liquid separation or to a water dilution before step (a).

4. The process according to claim 1, wherein no acid or base is added to the fermentation medium or the fraction thereof prior or during the demulsifying step (a).

5. The process according to claim 1, wherein in the demulsifying step, the pH range of the fermentation medium or the fraction thereof is from 2 to 7.

6. The process according to claim 1, wherein the surfactant is selected from an anionic surfactant and a non-ionic surfactant and their mixture.

7. The process according to claim 6, wherein the anionic surfactant is selected from sulfates and sulfonates and the nonionic surfactant is a polyether polyol.

8. The process according to claim 1, wherein the concentration of surfactant present in the fermentation medium or the fraction thereof in the demulsifying step (a) is from $5.10^{-3}$ to 1% v/v.

9. The process according to claim 1, wherein the concentration of salt present in the fermentation medium or the fraction thereof in the demulsifying step (a) is from 0.01 mol/L to 5 mol/L.

10. The process according to claim 1, wherein the fermentation medium or the fraction thereof is heated before being submitted to the separation step (b), after addition of the surfactant, at a heating temperature inferior to a temperature at which the isoprenoid compounds are degraded or decomposed.

11. The process according to claim 1, wherein the isoprenoid compound produced by fermentation is a C5-C20 isoprenoid.

12. The process according to claim 11, wherein the isoprenoid compound is a sesquiterpene.

* * * * *